United States Patent

Godwin

[11] Patent Number: 6,146,346
[45] Date of Patent: Nov. 14, 2000

[54] SPORTS BRACE

[76] Inventor: Andrew Godwin, 1936 Ambrosi Road, Kelowna, British Columbia, Canada, V1Y 4R9

[21] Appl. No.: 09/282,440

[22] Filed: Mar. 31, 1999

Related U.S. Application Data

[60] Provisional application No. 60/080,322, Apr. 1, 1998.

[30] Foreign Application Priority Data

Jan. 22, 1999 [CA] Canada ................................ 2259889

[51] Int. Cl.⁷ ....................................................... A61F 5/00
[52] U.S. Cl. ................................ 602/19; 602/4; 128/869; 128/875; 128/878
[58] Field of Search .................................. 602/5, 19, 20, 602/4, 60–63, 75; 128/878, 845, 869, 874–876, 95.1, 99.1, 105.1, DIG. 19; 2/44, 45

[56] References Cited

U.S. PATENT DOCUMENTS

| | | | |
|---|---|---|---|
| 2,543,847 | 3/1951 | Hallstedt | 602/4 |
| 4,198,964 | 4/1980 | Honneffer | 602/19 |
| 4,819,663 | 4/1989 | Matre | 128/876 |
| 4,844,306 | 7/1989 | Ruff et al. | 224/600 |
| 4,862,878 | 9/1989 | Davison et al. | 602/20 |
| 5,393,300 | 2/1995 | Bauerfeind et al. | 602/4 |
| 5,435,272 | 7/1995 | Epstein | 119/770 |
| 5,538,015 | 7/1996 | Povlson | 128/869 |
| 5,788,659 | 8/1998 | Haas | 602/20 |

*Primary Examiner*—Mickey Yu
*Assistant Examiner*—Denise Pothier
*Attorney, Agent, or Firm*—Antony C. Edwards

[57] ABSTRACT

A shoulder brace consists of a figure "8" strap tensioned between a lower loop anchored around a thigh and a collar or sleeve worn on an opposite upper arm corresponding to an injured shoulder so as to extend the upper loop diagonally across the torso, thereby immobilizing the upper arm to prevent shoulder abduction and external rotation after, for example, shoulder dislocation. The upper and lower loops crossover adjacent the hip, with lower loop snugged under the crotch so as to allow relatively unrestricted movement of the thigh, for example, during exercise. The shoulder brace is thus well adapted for use as a sports brace.

11 Claims, 6 Drawing Sheets

SPORTS BRACE

CROSS REFERENCE TO RELATED APPLICATION

This application claims priority from United States Provisional Patent Application No. 60/080,322 filed Apr. 1, 1998 titled Sports Brace.

FIELD OF THE INVENTION

This invention relates to the field of braces for immobilizing limbs, and in particular, to braces for immobilizing the upper arm and shoulder adapted for use by athletes.

BACKGROUND OF THE INVENTION

A common sports injury is a dislocated shoulder, torn shoulder muscles or the like. While the injury is recuperating, the injured person is prevented from activity which might risk re-injuring the shoulder unless the injured person is wearing a brace which limits the range of motion of the arm attached to the injured shoulder.

In the prior art, applicant is aware of U.S. Pat. No. 4,491,129 which issued Jan. 1, 1985 to Lockwood for a Strapping Assembly And Method For The Treatment Of Acromioclavicular Separations. The Lockwood assembly includes a high stocking worn on the leg of the patient on the opposite side of the separation injury, a strap connected at one end to the stocking and tensionable by means of a garter. The strap extends diagonally across the back from the stocking, over the shoulder on the side of the injury, and downwardly along the front of the chest to loop around the forearm beneath the shoulder. The forearm is thus supported in a sling-like position. What is neither taught nor suggested is the use of a figure "8" anchored around the upper thigh for immobilizing the contralateral upper arm following a shoulder dislocation injury rather than a clavicle separation.

Applicant is also aware of U.S. Pat. No. 4,735,198 which issued Apr. 5, 1988 to Sawa for an Injury Reduction and Stabilizing Harness. Sawa teaches a body harness -formed as a partial vest having a torso encircling portion and, extended from one side of the torso encircling portion, a sleeve for encircling the upper arm and shoulder. The upper arm within the sleeve may be immobilized by releasably mountable straps mountable to the sleeve and to the torso encircling portion. Again, what is neither taught nor suggested is the use of a figure "8" anchored around the upper thigh. Rather, it has been the applicant's experience that devices according to the Sawa design tend to ride up during use due to imperfect fit of the vest so as to uncomfortably rub against the ribs. It is also been found that during active use, the vest may be uncomfortably hot.

SUMMARY OF THE INVENTION

In summary, the shoulder brace of the present invention comprises a first elongate flexible member crossed over so as to form a lower loop along a mid portion of the first elongate flexible member. An upper vertex of the lower loop is formed at an adjustable crossover. The adjustable crossover is adjustable so as to snug the lower loop around an upper thigh of a user by sliding mating or releasable fastening of the first elongate flexible member in a criss-cross arrangement at first and second portions thereof corresponding to the crossover at the vertex of the lower loop.

An adjustable cuff is provided which is selectively adjustable for snug wearing around an upper arm of the user. First and second opposite ends of the first elongate flexible member are mounted, or releasably mountable, to the cuff so as to form an upper loop generally diagonally extending between the crossover and the cuff so as to tension the first elongate flexible member therebetween and thereby form a figure "8" of the first elongate flexible member.

The upper loop, when tensioned between the crossover and the cuff extends diagonally across front and back surfaces of a torso of the user so as to encircle the torso within the upper loop. The upper loop lies generally in a first plane angularly offset from a second plane generally containing the lower loop. The planes intersect at the crossover when the lower loop is worn around the upper thigh of the user, opposite to an injured of the user, and the cuff is worn on the upper arm on a side of the user corresponding to the injured shoulder.

A second elongate flexible member may be mounted or mountable generally perpendicular to the upper loop so as to extend in a supporting loop from a side of the upper loop adjacent the front surface of the torso to a side of the upper loop adjacent the back surface of the torso. The second elongate flexible member may be mounted so as to extend over an opposite shoulder of the user to the injured shoulder and tensioned so as to support the upper loop in generally the first plane.

When the lower loop is worn around the upper thigh with the crossover located generally adjacent a hip of the user corresponding to the upper thigh, and the upper loop extends diagonally from the crossover across the torso so as to be tensioned to or around the cuff on the upper arm on the side of the user corresponding to the injured shoulder, the upper arm is immobilized.

The adjustable cuff may be adjustable by means of first releasable fasteners mounted at opposite ends of the cuff. The first and second opposite ends of the first elongate flexible member may be releasably mountable to the cuff by means of second hook and loop fasteners.

The means of sliding mating or releasable fastening of the adjustable crossover may include at least one restraining strap fastened at its ends to the first portion of the first elongate flexible member so as to sandwich, at the crossover, the second portion of the first elongate flexible member in sliding engagement therebetween. The first portion is spaced from the second portion of the first elongate flexible member to thereby form the lower loop. Advantageously, a second restraining strap is mounted at its ends to the second portion of the elongate flexible member so as to sandwich, at the crossover, the first portion therebetween. The first portion may be in sliding engagement therebetween or releasably fastened therebetween for example, by use of hook and loop fasteners.

Further advantageously, the first elongate flexible member and the second elongate flexible member are straps.

DETAILED DESCRIPTION OF THE
PREFERRED EMBODIMENT

Figure 1:
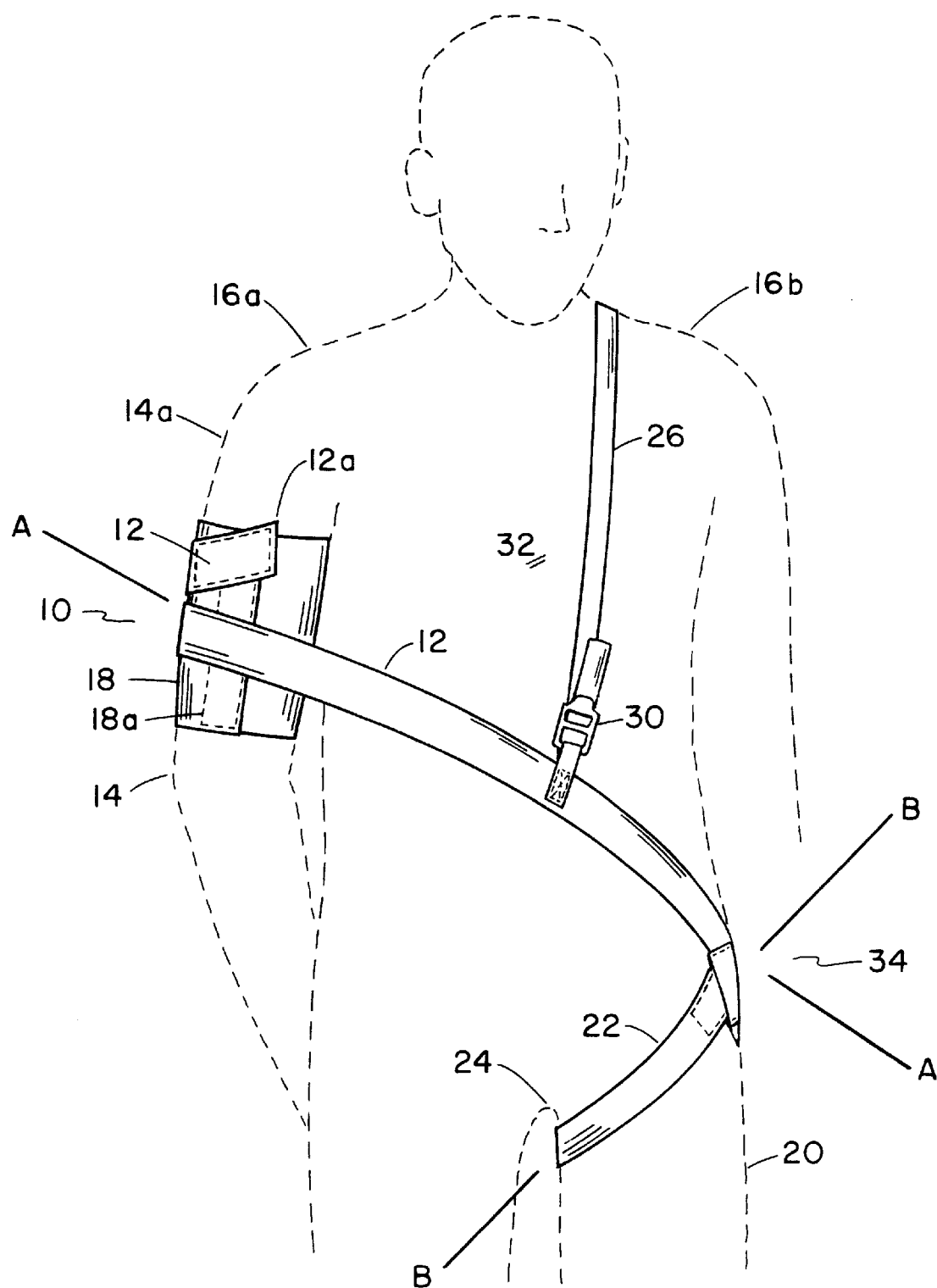
FIG. 1 is, in front elevation view, the sports brace of the present invention being worn by a patient.
Figure 2:
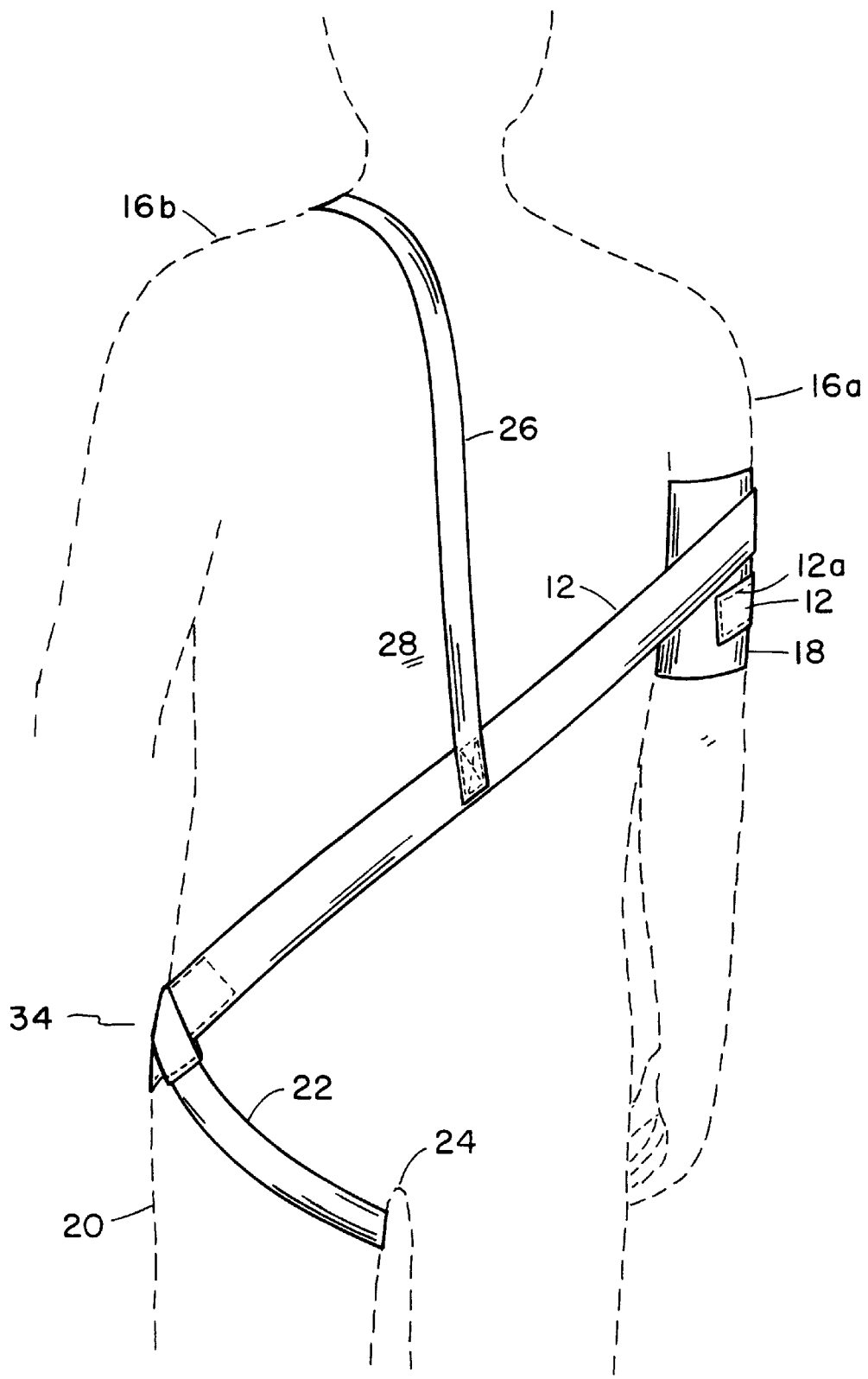
FIG. 2 is, in rear elevation view, the sports brace of FIG. 1.
Figure 3:
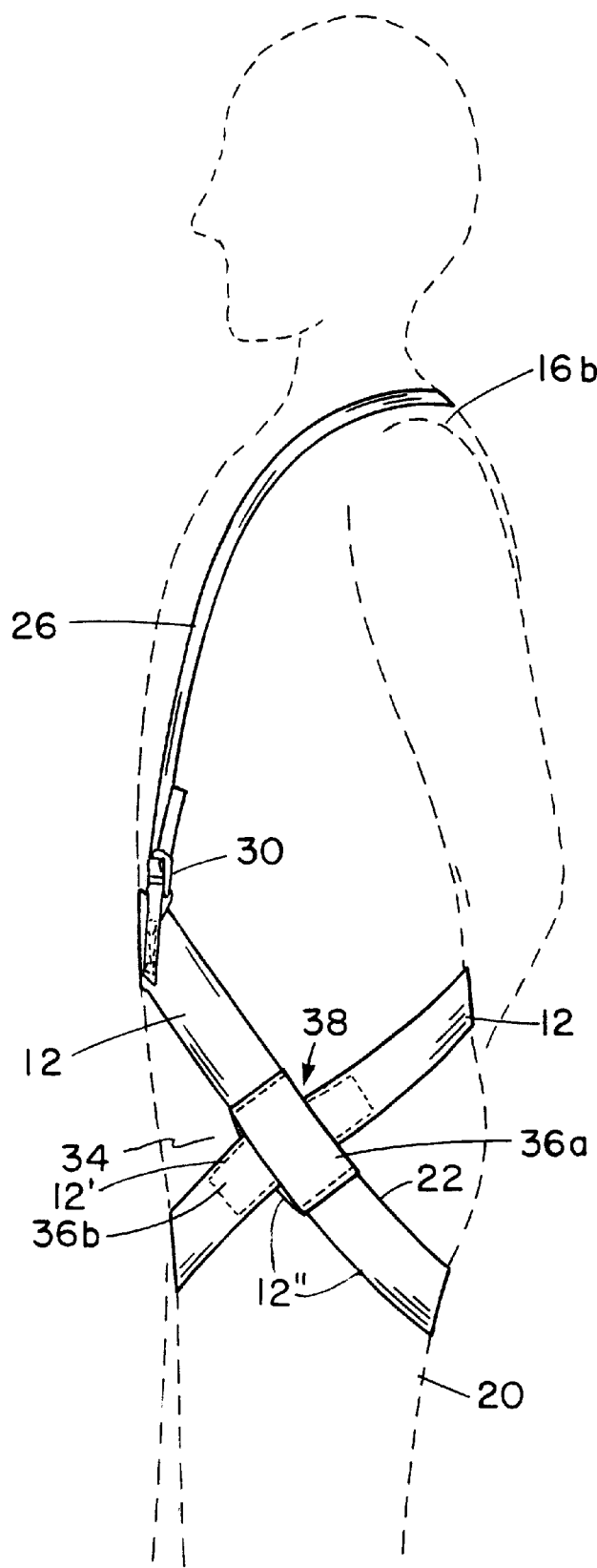
FIG. 3 is, in right side elevation view, the sports brace of FIG. 1.

As seen in FIGS. 1–3, the shoulder brace of the present invention is a simple yet effective flexible structure 10 which uses a first elongate strap 12 which wraps around the arm 14, below the shoulder 16a and preferably around a collar or sleeve 18 on the upper arm 14a, and around the thigh 20 of the user in the manner of a figure "8". Wrapping the lower loop 22 of the figure "8" around thigh 20 snugly up under crotch 24 provides two advantages, namely, the brace does not ride up so as to thereby defeat the immobilizing effect on the upper arm 14a, and the use of thigh 20, for example, in running is not interfered with.

An upper loop in the figure "8", which may be thought of as lying generally in plane A—A shown in FIG. 1, is formed by releasably mounting, in opposed relation, the opposite ends of first elongate strap 12 to collar or sleeve 18. Strap 12 may be releasably mounted for example by means of hook and loop fasteners 12a (shown in dotted outline) on the ends of strap 12, and corresponding mating pieces on the exterior surface of collar or sleeve 18. Collar or sleeve 18 may be snugly fitted around the bicep area of upper arm 14a by means of hook and loop fasteners 18a.

A second shorter elongate flexible strap 26 is joined in the manner of a distorted "T" towards one end of, so as to extend at an angle between 45 and 90 degrees from, the first elongate longer strap 12. The shorter strap 26 supports the upper loop in the figure "8" by extending over the non-injured shoulder 16b and prevents the upper loop of the figure "8" from slipping or drooping. Strap 26 may be joined to strap 12 by means of stitching or the like, preferably to place the stitched end of strap 26 in the middle of torso back 28. The opposite end of strap 26 is mounted, is releasably mountable by means of buckle 30 or other releasable fasteners, to strap 12 advantageously in the middle of torso front 32. Buckle 30 may be stitched to strap 12. Strap 26 may be adjustable in length, or pre-adjusted or sized so that strap 12 lies generally in a plane A—A where strap 12 crosses torso back 28 and torso front 32.

Figure 3A:
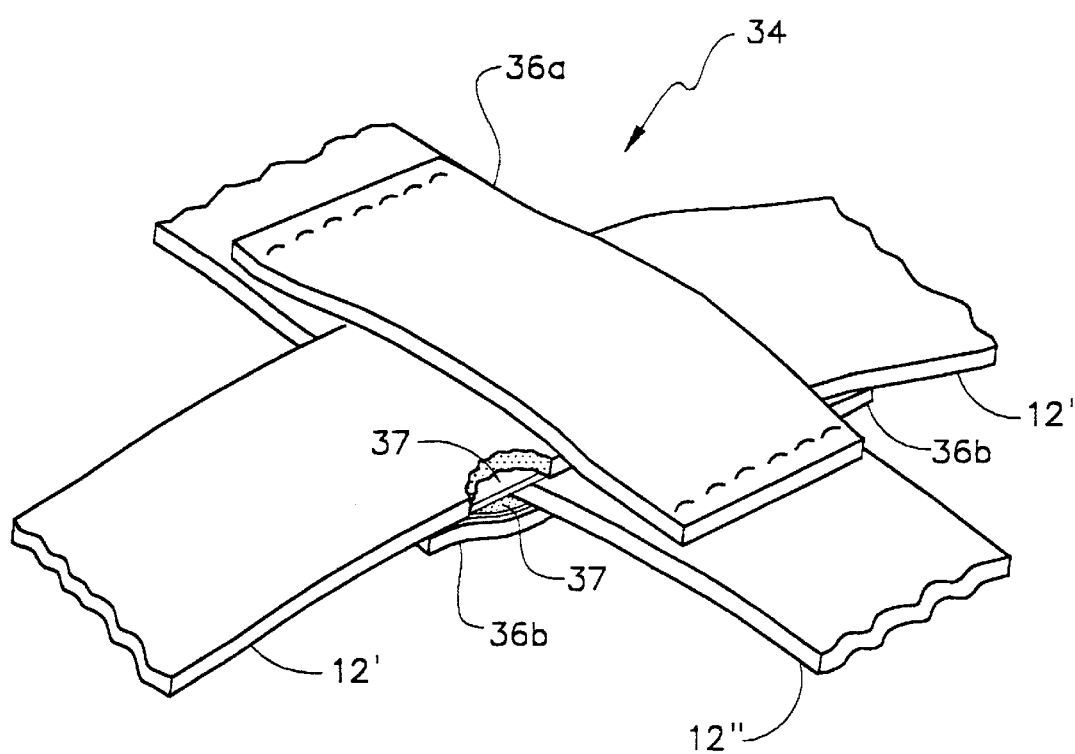
FIG. 3a is, in enlarged partially cutaway perspective view, an alternative embodiment of the hip cross-over of the sports brace of the present invention incorporating a hook and loop fastener.
Figure 4:
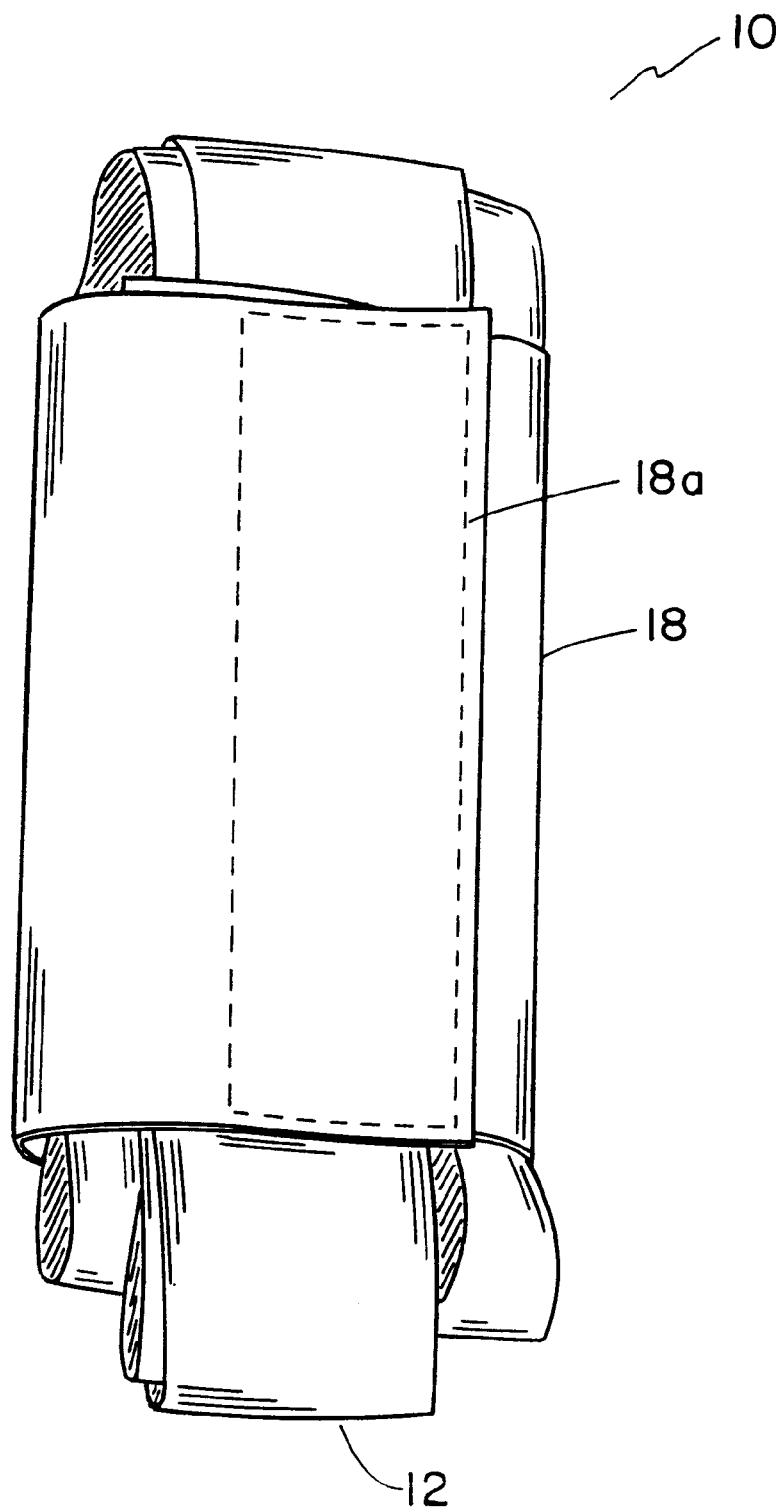
FIG. 4 is, in perspective view, the sports brace of the present invention in a storage configuration.

The upper and lower loops of the figure "8" formed by strap 12 intersect at adjustable crossover 34 so as to form an "X"-shape when viewed in side elevation. The lower loop may be thought of as lying generally in plane B—B, angularly offset from plane A—A and intersecting at the crossover 34. Crossover 34 is adjustable in the sense that strap 12 may be snugged around thigh 20 when adjusting the tension of strap 12 and, tensioned against collar or sleeve 18 when strap 12 is mounted thereto. The lower loop can be snugged around thigh 20 and held in a tight loop by hook and loop fasteners 37 as seen in FIG. 3a. Crossover 34 may be adjustable by means of restraining straps 36a and 36b (restraining strap 36b shown in dotted outline) mounted as by stitching at the ends thereof to corresponding portions of strap 12 at crossover 34. Restraining strap 36a sandwiches strap segment 12' of strap 12 in sliding engagement between restraining strap 36a (shown lying on top of segment 12' in FIG. 3) and strap segment 12" (shown looping under segment 12' in FIG. 3), thus limiting the range of motion of strap segment 12' along strap segment 12". Restraining strap 36b is mounted to the underside of crossover 34, where crossover 34 is advantageously adjacent the user's hip 38. Restraining strap 36b sandwiches strap segment 12" in sliding engagement, or in releasably secured engagement by means of hook and loop fasteners at crossover 34, such as seen in FIG. 3a between restraining strap 36b and strap segment 12', thus limiting the range of motion of strap segment 12" along strap segment 12'.

The result is that the figure "8" of strap 12, tensioned between the lower loop 22 anchored around thigh 20 and collar or sleeve 18, does not pull on injured shoulder 16a while immobilizing upper arm 14a so as to prevent shoulder abduction and external rotation after, for example, shoulder dislocation. The placement of crossover 34 adjacent hip 38, with lower loop 22 snugged under crotch 24, allows relatively unrestricted movement of thigh 20, for example, during exercise. Consequently, shoulder brace 10 is well adapted for use as a sports brace.

Figure 5:
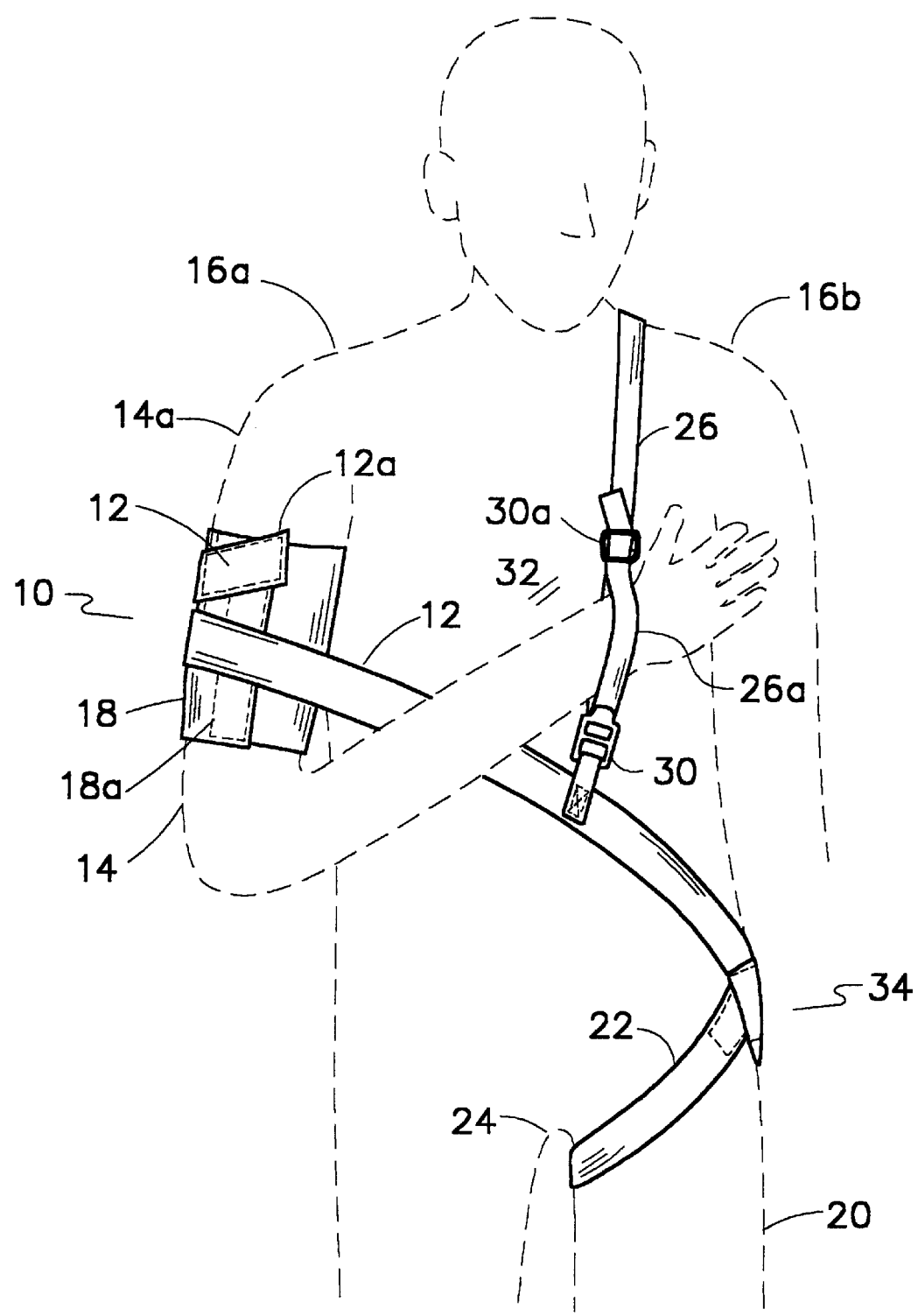
FIG. 5 is an alternative embodiment of the sports brace of FIG. 1.

As seen in FIG. 5, the sports brace may in an alternative embodiment include a means for immobilizing the shoulder. In particular, strap 26 is left longer than in the embodiment of FIGS. 1–4 and is releasably adjustably fastened back onto itself by a second buckle 30a. The extra length 26a of strap 26 extends, adjustably, between buckles 30 and 30a so as to form a loop which may be snugged to retain the wrist therein, thereby assisting in immobilizing the shoulder.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A shoulder brace comprising a first elongate flexible member forming a lower loop along a mid portion of said first elongate flexible member, an upper vertex of said lower loop formed at an adjustable crossover, said adjustable crossover adjustable so as to snug said lower loop around an upper thigh of a user by mating of said first elongate flexible member at first and second portions thereof corresponding to said crossover at said vertex of said lower loop, an adjustable cuff, selectively adjustable for snug wearing around an upper arm of the user, first and second opposite free ends of said first elongate flexible member releasably mounted to said cuff so as to form an upper loop diagonally extending between said crossover and said cuff so as to tension said First elongate flexible member therebetween and thereby form a figure "8" of said first elongate flexible member, said upper loop, when tensioned between said crossover and said cuff, extending generally diagonally across front and back surfaces of a torso of the user so as to encircle the torso within said upper loop, said upper loop lying generally in a first plane angularly offset from a second plane generally containing said lower loop and intersecting at said crossover when said lower loop is worn around the upper thigh of the user opposite to an injured shoulder of the user, and said cuff worn on the upper arm on a side of the user corresponding to the injured shoulder when in use, wherein, when said lower loop is worn around the upper thigh with said crossover located generally adjacent a hip of the user corresponding to the upper thigh when in use, and said upper loop extends diagonally from said crossover across the torso so as to be tensioned around said cuff on the upper arm on the side of the user corresponding to the injured shoulder when in use, and tensioned so as to support said upper loop in generally said first plane, the upper arm is immobilized.

2. The shoulder brace of claim 1 wherein said adjustable crossover is adjustable with a means for sliding mating said first elongate flexible member at said first and second portions thereof.

3. The shoulder brace of claim 2 wherein said means for sliding mating said adjustable crossover comprises at least one restraining strap fastened at its ends to said first portion of said first elongate flexible member so as to sandwich, at said crossover, said second portion of said first elongate flexible member in sliding engagement therebetween, said first portion spaced from said second portion of said first elongate flexible member to thereby form said lower loop.

4. The shoulder brace of claim 3 wherein said first elongate flexible member is a strap.

5. The shoulder brace of claim 1 wherein said adjustable crossover is adjustable with a means for releasably fastenable mating said first elongate flexible member at said first and second portions thereof.

6. The shoulder brace of claim 1 further comprising a second elongate flexible member mounted to said upper loop, generally perpendicular to said upper loop so as to extend in a supporting loop, when in use, from a side of said upper loop adjacent the front surface of the torso to a side of said upper loop adjacent the back surface of the torso, wherein said second elongate flexible member is mounted generally perpendicularly to said upper loop so as to extend, when in use, over an opposite shoulder of the user to the injured shoulder.

7. The shoulder brace of claim 6 wherein said adjustable crossover is adjustable with a means for sliding mating said first elongate flexible member at said first and second portions thereof.

8. The shoulder brace of claim 6 wherein said adjustable crossover is adjustable with a means for releasably fastenable mating said first elongate flexible member at said first and second portions thereof.

9. The shoulder brace of claim 6 wherein said first and second elongate flexible members are straps.

10. The shoulder brace of claim 1 wherein said adjustable cuff is adjustable by means of first releasable fasteners mounted at opposite ends of said cuff.

11. The shoulder brace of claim 1 wherein said first and second opposite free ends of said first elongate flexible member are releasably mounted to said cuff by means of second hook and loop fasteners.

* * * * *